(12) United States Patent
Kamohara et al.

(10) Patent No.: US 8,420,712 B2
(45) Date of Patent: Apr. 16, 2013

(54) DENTAL SILICONE IMPRESSION MATERIAL COMPOSITION

(75) Inventors: Hiroshi Kamohara, Itabashi-ku (JP); Shouichi Fukushima, Itabashi-ku (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 13/248,249

(22) Filed: Sep. 29, 2011

(65) Prior Publication Data

US 2012/0083549 A1    Apr. 5, 2012

(30) Foreign Application Priority Data

Sep. 30, 2010  (JP) ................. 2010-220368

(51) Int. Cl.
| | |
|---|---|
| A61K 6/10 | (2006.01) |
| C08G 77/20 | (2006.01) |
| C08G 77/04 | (2006.01) |
| C08G 77/12 | (2006.01) |
| A61C 9/00 | (2006.01) |
| C08L 83/05 | (2006.01) |

(52) U.S. Cl.
USPC ............. 523/109; 433/214; 528/15; 528/31; 528/32; 528/33; 524/588; 525/478

(58) Field of Classification Search .......... 523/109; 433/214; 528/15, 31, 32, 33; 525/478
See application file for complete search history.

(56) References Cited

U.S. PATENT DOCUMENTS

| | | | |
|---|---|---|---|
| 4,609,687 A * | 9/1986 | Schwabe et al. ............. | 523/109 |
| 4,879,339 A | 11/1989 | Yoshino et al. | |
| 5,066,714 A | 11/1991 | Inoue et al. | |
| 2004/0110863 A1 * | 6/2004 | Zech et al. .................... | 523/109 |
| 2006/0281856 A1 * | 12/2006 | Kollefrath et al. ............ | 524/588 |
| 2010/0227946 A1 * | 9/2010 | Fetz ............................... | 523/109 |
| 2011/0039973 A1 * | 2/2011 | Kopp et al. .................... | 523/109 |

FOREIGN PATENT DOCUMENTS

| | | |
|---|---|---|
| EP | 1 475 069 A1 | 11/2004 |
| GB | 2 314 849 A | 1/1998 |
| JP | 10-072307 | 3/1998 |
| JP | 2009-203196 | 9/2009 |

OTHER PUBLICATIONS

European Search Report dated Nov. 14, 2011, issued in corresponding application No. EP 11 00 7946.

* cited by examiner

*Primary Examiner* — Michael Pepitone
(74) *Attorney, Agent, or Firm* — Oblon, Spivak, McClelland, Maier & Neustadt, L.L.P.

(57) ABSTRACT

To provide a silicone impression material having high viscosity of a kneaded material before curing and low hardness after curing. A dental silicone impression material composition includes:

A) an organopolysiloxane mixture comprising a) an organopolysiloxane having at least two aliphatic unsaturated hydrocarbons in one molecule and having viscosity of 1,000,000 mPa·s or more at 25° C., and b) an organopolysiloxane having at least one aliphatic unsaturated hydrocarbon in one molecule and having viscosity of 100 to 5,000 mPa·s at 25° C., wherein a ratio of a):b) is 1:0.5 to 10;

B) an organohydrogenpolysiloxane having at least three hydrogen atoms directly bonded to a silicon atom in one molecule;

C) a silicone-soluble platinum compound;

D) an organopolysiloxane not having a functional group; and

E) an inorganic filler.

1 Claim, No Drawings

DENTAL SILICONE IMPRESSION MATERIAL COMPOSITION

BACKGROUND OF THE INVENTION

1. Field of the Invention

The present invention relates to a silicone impression material used when producing a dental prosthesis in dentistry. More particularly, the present invention relates to a dental silicone impression material composition having high viscosity of a kneaded material before curing and low hardness after curing.

2. Description of the Conventional Art

In a dental treatment, a silicone impression material including a silicone resin as a main component, an alginate impression material containing alginate as a main agent, calcium sulfate as a curing material, which is cured under the existence of water, and a polyether-based impression material including a polyether resin as a main component have been used.

According to the aging of population, a necessity of dental treatments at home has increased. In the home dental treatments, the alginate impression material has been widely used, because the alginate impression material has low cost, can be easily removed from an oral cavity because of having low hardness, and can be applied to a complicated row of teeth of a patient. Further, since there are many old people whose vomiting reflex is weak, the alginate impression material having high viscosity of a kneaded material and hardly flowing into the depth of a throat has been preferably used. The alginate impression material shrinks by drying and impression accuracy decreases. For preventing this tendency, it is necessary to rapidly pour gypsum into the material after taking impression. However, since bringing materials or tools for pouring the gypsum is complicated, the alginate impression material has not been proper for a home treatment. Accordingly, developing a silicone impression material having similar characteristics to the alginate impression material has been desired, that is, high viscosity of a kneaded material before curing so as to hardly flow into the depth of a throat, and low hardness after curing which is a similar level to the alginate impression material.

Furthermore, when a dental technician produces a dental prosthesis with high accuracy, a silicone impression material having higher accuracy than the alginate impression material has been used. However, since the conventional silicone impression material has high hardness after curing, an operation for sealing an undercut of a surplus part with wax or the like and thereby easily removing the silicone impression material after curing from an oral cavity is necessary. More specifically, currently, since the number of a patient suffering from periodontitis even though having many remaining teeth has been increasing, an operation for treating the undercut more accurately and minutely has been necessary. Therefore, a silicone impression material which does not need the undercut treatment, namely, a silicone impression material having low hardness after curing and being easily removed from an oral cavity has been desired.

As a method for solving the aforementioned problems of the conventional silicone impression material, a composition for a dental impression which can prevent dropping of a kneaded material has been discussed (refer to Japanese Patent Application Laid-Open No. 2009-203196), and the composition is produced by adding hydrocarbon-based oily components to a composition including an organosiloxane having a specific structure, a polyether, an organohydrogenpolysiloxane, an inorganic filler, a nonionic surfactant, and a silicone-soluble platinum compound. Further, a silicone composition for a dental impression has been discussed (refer to Japanese Patent Application Laid-Open No. H10-72307), and the silicone composition includes an organopolysiloxane having a specific structure, an organohydrogenpolysiloxane, a silicone-soluble platinum compound, a fine powdery silica having a specific surface area and being subjected to hydrophobic treatment and a methylphenyl polysiloxane. However, although these impression materials do not cause dropping of a kneaded material, these impression materials have low viscosity of the kneaded material before curing because of including the hydrocarbon-based oily components with low viscosity. Thus, since an oral mucosa cannot be fully pressurized, the accuracy of the impression is insufficient.

SUMMARY OF THE INVENTION

An objective of the present invention is to provide a silicone impression material having high viscosity of a kneaded material before curing and low hardness after curing.

Namely, according to an aspect of the present invention, a dental silicone impression material composition comprises A) 100 weight parts of a mixed material of organopolysiloxane, B) 0.1 to 100 weight parts of an organohydrogenpolysiloxane with respect to 100 weight parts of A), C) 10 ppm to 1 weight part of a silicone-soluble platinum compound with respect to the total amount of the above two components A) and B), D) 1 to 50 weight parts of an organopolysiloxane with respect to 100 weight parts of A), and E) 10 to 100 weight parts of an inorganic filler with respect to 100 weight parts of A). The mixed material of organopolysiloxane A) includes a) an organopolysiloxane having at least two aliphatic unsaturated hydrocarbons in one molecule and having viscosity of 1,000,000 mPa·s or more at 25° C., and b) an organopolysiloxane having at least one aliphatic unsaturated hydrocarbon in one molecule and having viscosity of 100 to 5,000 mPa·s at 25° C. The ratio of a):b) in the organopolysiloxane in A) component is 1:0.5 to 10. The organohydrogenpolysiloxane in B) component has at least three hydrogen atoms directly bonded to a silicon atom in one molecule. The organopolysiloxane in D) component has not a functional group.

The dental silicone impression material composition according to the present invention has higher viscosity of a kneaded material before curing than conventional dental silicone impression materials and hardly flows into the depth of a throat. Thus, the dental silicone impression material composition according to the present invention can be used to clinical cases such as a home treatment and the like in which the alginate impression material has been conventionally used. In addition, there is an advantage that the dental silicone impression material composition according to the present invention has proper accuracy of impression because of having high viscosity of a kneaded material before curing. Nevertheless, since the hardness after curing is low, the impression material can be removed easily. Thus, the dental silicone impression material composition can be used to clinical cases such as a home treatment and the like. Furthermore, the dental silicone impression material composition does not need an undercut treatment even in usual use, so that it is an excellent impression material composition.

The organopolysiloxane used as the component A) for the dental silicone impression material composition according to the present invention is a mixed material of two different kinds. Among them, an organopolysiloxane crude rubber a) has at least two aliphatic unsaturated hydrocarbons in one molecule and has viscosity of 1,000,000 mPa·s or more at 25° C. The crude rubber is an organopolysiloxane having a puttylike property at a room temperature and a polymerization degree of 2,000 or more. The organopolysiloxane has at least two aliphatic unsaturated hydrocarbons in one molecule. More specifically, it is preferable that molecular chain terminals (of the organopolysiloxane) are blocked with a vinyl silyl group. In this case, the molecular chain can have a plurality of terminal vinyl groups, and a vinyl group can be included in the molecular chain. The aliphatic unsaturated hydrocarbon can include a plurality of terminal vinyl groups or can include a vinyl group in a chain. Further, the present organopolysiloxane molecular chain in a) includes an alkyl group such as a methyl group, an ethyl group, or the like, a phenyl group, a tolyl group, or the like. Particularly, a methyl group or a phenyl group is preferable.

The organopolysiloxane b) used with the component a) at a specific ratio has at least one aliphatic unsaturated hydrocarbon in one molecule and has viscosity of 100 to 5,000 mPa·s at 25° C. The organopolysiloxane b) is a liquid organopolysiloxane having a totally different state at 25° C., comparing with the component a). The organopolysiloxane includes at least one aliphatic unsaturated hydrocarbon in one molecule. More specifically, like a), it is preferable that molecular chain terminals (of the organopolysiloxane) are blocked with a vinyl silyl group. In this case, the molecular chain can have a plurality of terminal vinyl groups, and a vinyl group can be included in the molecular chain. Further, the present organopolysiloxane molecular chain in b) includes an alkyl group such as a methyl group, an ethyl group or the like, a phenyl group, a tolyl group, or the like. Particularly, a methyl group or a phenyl group is preferable.

The ratio of a):b) in the component A) is 0.5:10, and preferably, 1:1 to 3.

The organohydrogenpolysiloxane having at least three hydrogen atoms directly bonded to a silicon atom in one molecule works as a cross-linking material in the component A). The hydrogen atoms directly bonded to the silicon atom in the component B) can exist at a molecular chain terminal or a side chain. However, preferably, the hydrogen atoms exist at both terminals of a molecular chain. Further, the blending ratio of the component B) is 0.1 to 100 weight parts with respect to 100 weight parts of the component A), and preferably, 1 to 50 weight parts. If the blending ratio is less than 0.1 weight parts, the hardness of a cured body decreases, and a curing rate comes to be slow. If the blending ratio exceeds 100 weight parts, a cured body comes to be brittle too much. When the dental impression material composition according to the present invention is provided in a two components form of a base paste and a catalyst paste including the component C), which will be described in detail below, the component B) is not blended in the catalyst paste in light of preservation stability.

The silicone-soluble platinum compound as the component C) works as a catalyst for cross-linking and polymerizing the component A) and the component B). More particularly, chloroplatinic acid, alcohol-modified chloroplatinic acid, a complex of chloroplatinic acid and olefin, or the like can be used. The most preferable compound is a vinylsiloxane complex of chloroplatinic acid. An adding amount of such the compound is within a range from 10 to 500 ppm with respect to the total amount of the components of A) and B). If the addition amount is less than 10 ppm, a curing rate is slow. Further, there is a disadvantage that when a slight amount of a material preventing a catalytic ability of the platinum compound exists, the curing rate comes to be slow. If the adding amount exceeds 500 ppm, a curing rate is too fast and, in addition, a production cost increases, so that it is not appropriate. It is preferable that the silicone-soluble platinum compound such as chloroplatinic acid, or the like is used by being dissolved with an alcohol-base, a ketone-base, an ether-base, or a hydrocarbon-base solvent, polysiloxane oil, or the like.

As the organopolysiloxane not having a functional group as the component D), dimethylpolysiloxane, methylphenylpolysiloxane, or modified silicone oil can be used. The organopolysiloxane not having a functional group as the component D) does not react with the components A), B), and C). The viscosity of the organopolysiloxane used as the component D) at 25° C. is 30 to 500,000 mPa·s, and preferably 100 to 10,000 mPa·s. The content ratio of the organopolysiloxane not having a functional group as the component D) is 1 to 50 weight parts with respect to 100 weight parts of the component A), and preferably, 5 to 20 weight parts.

The inorganic filler as the component E) improves operability of the dental silicone impression material composition before curing and properties after curing. The component E) could be, for example, powders of quartz, cristobalite, diatomite, fused quartz, glass fibers, titanium dioxide, fumed silica, or the like. The blending ratio of the inorganic filler is 10 to 100 weight parts with respect to 100 weight parts of the component A). If the blending ratio is less than 10 weight parts, flowability of a kneaded material before curing comes to be too high. If the blending ratio exceeds 100 weight parts, viscosity of the kneaded material before curing comes to be too high, so that a kneading operation comes to be hard.

In the dental silicone impression material composition according to the present invention, various kinds of inorganic or organic colorants, liquid hydrocarbons, nonionic surfactants, polyether compounds, or silicone resins can be used within a range not preventing the properties of the composition.

DETAILED DESCRIPTION OF PREFERRED EMBODIMENT

Preferred embodiments of the present invention will be described in detail below, but the present invention is not limited in these embodiments.

Example 1

Base Paste

A)
a) A dimethylpolysiloxane crude rubber having a viscosity of 10,000,000 mPa·s at 25° C. and having a vinyl valence of 0.002 mol/100 g. b) A dimethylpolysiloxane wherein both molecular chain terminals are blocked with a methylvinylsiloxy group and having a viscosity of 1,000 mPa·s at 25° C.

| | |
|---|---|
| a):b) = 1:1.5 | 100 weight parts |
| A linear methylhydrogenpolysiloxane containing 40 mol % of a methylhydrogensiloxane unit: | 10 weight parts |
| A dimethylpolysiloxane having a viscosity of 1,000 mPa · s at 25° C. | 20 weight parts |
| Quartz | 30 weight parts |

(Catalyst Paste)
A)
a) A dimethylpolysiloxane crude rubber having a viscosity of 10,000,000 mPa·s at 25° C. and having a vinyl valence of 0.002 mol/100 g. b) A dimethylpolysiloxane wherein both molecular chain terminals are blocked with a methylvinylsiloxy group and having a viscosity of 1,000 mPa·s at 25° C.

| | |
|---|---|
| a):b) = 1:1.5 | 100 weight parts |
| A silicone oil solution containing 0.6% by weight of a platinum complex of 1,3-divinyltetramethyl-disiloxane: | 1 weight part |
| A dimethylpolysiloxane having a viscosity of 1,000 mPa·s at 25° C. | 20 weight parts |
| Quartz | 30 weight parts |

A base paste and a catalyst paste were produced by vacuum-stirring the aforementioned each component by a planetary mixer.

<Measurement of Hardness>

For measuring hardness of the cured body, 4 g of the base paste and 4 g of the catalyst paste were kneaded for 30 seconds, and the kneaded material was poured into a metal ring (having an inner diameter of 24 mm and a height of 8 mm). Then, the upper and lower sides of the metal ring were clamped by a glass plate, and the metal ring was dipped for 2 minutes in water at 35° C. After two minutes, the metal ring was taken out from water, demolded, and then taken out. After 1 minute, the hardness of the cured body was measured by using a durometer hardness meter A type (produced by KOBUNSHI KEIKI CO., LTD.). These results were shown in Table 1 collectively.

<Measurement of Elastic Strain>

4 g of each of the paste and the catalyst paste was weighed and kneaded like the measurement of the hardness. Then, elastic strain and permanent strain were measured by holding the kneaded materials in an oral cavity for 4 minutes according to JIS T 6513 (2005). These results were shown in Table 1 collectively.

<Measurement of Viscosity of Kneaded Materials>

4 g of each of the base paste and the catalyst paste was weighed and kneaded like the measurement of the hardness. Then, viscosity after 1 minute from the beginning of kneading was measured at 10 rpm by a B type viscometer (produced by TOKI SANGYO CO., LTD). These results were shown in Table 1 collectively. For comparing with the above kneaded material, viscosity of a kneaded material of an alginate impression material was also measured. In this measurement of the viscosity, a kneaded material to be used was produced by using a commercial alginate impression material (product name: AROMA FINE PLUS, produced by GC Corporation) and kneading the material with 16.8 g of powders and 40 ml of water for 20 seconds. After 1 minute from the beginning of kneading, the viscosity was measured.

<Comparison Test of Easiness of Removing Impression Material>

For confirming an easiness of removing the impression material after curing, an equal amount of the base paste and the catalyst paste was kneaded, and the kneaded material was built on a commercial tray (product name: IMPRESSION TRAY, produced by GC Corporation). Then, the tray was pressed to an upper jaw model (Produced by Nissin Dental Products INC.) and held for 2 minutes in water at 35° C. Then, the tray was removed from the model together with the impression material. Then, a kneaded material was produced by using a commercial alginate impression material (product name: AROMA FINE PLUS, produced by GC Corporation) and kneading the material with 16.8 g of powders and 40 ml of water for 20 seconds, and examples and comparative examples were compared by using the kneaded material. These results were shown in Table 1.

Example 2

Base Paste

A)
a) A dimethylpolysiloxane crude rubber having a viscosity of 7,000,000 mPa·s at 25° C. and having a vinyl valence of 0.0015 mol/100 g. b) A dimethylpolysiloxane wherein both molecular chain terminals are blocked with a methylvinylsiloxy group and having a viscosity of 1,500 mPa·s at 25° C.

| | |
|---|---|
| a):b) = 1:2 | 100 weight parts |
| A linear methylhydrogenpolysiloxane containing 50 mol % of a methylhydrogensiloxane unit: | 30 weight parts |
| A dimethylpolysiloxane having a viscosity of 2,000 mPa·s at 25° C. | 40 weight parts |
| Quartz | 70 weight parts |

(Catalyst Paste)
A)
a) A dimethylpolysiloxane crude rubber having a viscosity of 10,000,000 mPa·s at 25° C. and having a vinyl valence of 0.002 mol/100 g. b) A dimethylpolysiloxane wherein both molecular chain terminals are blocked with a methylvinylsiloxy group and having a viscosity of 1,000 mPa·s at 25° C.

| | |
|---|---|
| a):b) = 1:1.5 | 100 weight parts |
| A silicone oil solution containing 0.6% by weight of a platinum complex of 1,3-divinyltetramethyl-disiloxane | 1 weight part |
| A dimethylpolysiloxane having a viscosity of 2,000 mPa·S at 25° C. | 40 weight parts |
| Quartz | 70 weight parts |

A base paste and a catalyst paste were produced by vacuum-stirring the aforementioned each component by a planetary mixer. These base paste and catalyst paste were subjected to the same tests as Example 1. These results were shown in Table 1.

Example 3

Base Paste

A)
a) A dimethylpolysiloxane crude rubber having a viscosity of 15,000,000 mPa·s at 25° C. and having a vinyl valence of 0.0018 mol/100 g. b) A dimethylpolysiloxane wherein both molecular chain terminals are blocked with a methylvinylsiloxy group and having a viscosity of 600 mPa·s at 25° C.

| | |
|---|---|
| a):b) = 1:3 | 100 weight parts |
| A linear methylhydrogenpolysiloxane containing 45 mol % of a methylhydrogensiloxane unit | 15 weight parts |
| A dimethylpolysiloxane having a viscosity of 3,000 mPa·S at 25° C. | 15 weight parts |
| Quartz | 50 weight parts |

(Catalyst Paste)
A)
a) A dimethylpolysiloxane crude rubber having a viscosity of 10,000,000 mPa·s at 25° C. and having a vinyl valence of 0.0018 mol/100 g. b) A dimethylpolysiloxane wherein both molecular chain terminals are blocked with a methylvinylsiloxy group and having a viscosity of 600 mPa·s at 25° C.

| | |
|---|---|
| a):b) = 1:3 | 100 weight parts |
| A silicone oil solution containing 0.8% by weight of a platinum complex of 1,3-divinyltetramethyl-disiloxane | 1 weight part |
| A dimethylpolysiloxane having a viscosity of 2,000 mPa·s at 25° C. | 15 weight parts |
| Quartz | 50 weight parts |

A base paste and a catalyst paste were produced by vacuum-stirring the aforementioned each component by a planetary mixer. These base paste and catalyst paste were subjected to the same tests as Example 1. These results were shown in Table 1.

Example 4

Base Paste

A)
a) A dimethylpolysiloxane crude rubber having a viscosity of 10,000,000 mPa·s at 25° C. and having a vinyl valence of 0.003 mol/100 g. b) A dimethylpolysiloxane wherein both molecular chain terminals are blocked with a methylvinylsiloxy group and having a viscosity of 1,000 mPa·s at 25° C.

| | |
|---|---|
| a):b) = 1:2 | 100 weight parts |
| A linear methylhydrogenpolysiloxane containing 45 mol % of a methylhydrogensiloxane unit: | 20 weight parts |
| Dimethylpolysiloxane having a viscosity of 1,000 mPa·s at 25° C. | 10 weight parts |
| Quartz | 20 weight parts |
| Polyoxyethylene alkyl ether | 1 weight part |
| Polyethylene glycol diallyl ether wherein both molecular chain terminals are blocked with a vinyl group: | 0.5 weight parts |

(Catalyst Paste)
A)
a) A dimethylpolysiloxane crude rubber having a viscosity of 10,000,000 mPa·s at 25° C. and having a vinyl valence of 0.003 mol/100 g. b) A dimethylpolysiloxane wherein both molecular chain terminals are blocked with a methylvinylsiloxy group and having a viscosity of 1,000 mPa·s at 25° C.

| | |
|---|---|
| a):b) = 1:2 | 100 weight parts |
| A silicone oil solution containing 0.8% by weight of a platinum complex of 1,3-divinyltetramethyl-disiloxane: | 1 weight part |
| A dimethylpolysiloxane having a viscosity of 1,000 mPa·s at 25° C. | 15 weight parts |
| Quartz | 20 weight parts |

A base paste and catalyst paste were produced by vacuum-stirring the aforementioned each component by a planetary mixer. These base paste and catalyst paste were subjected to the same tests as Example 1. These results were shown in Table 1.

Comparative Example 1

Base Paste

| | |
|---|---|
| A dimethylpolysiloxane wherein both molecular chain terminals are blocked with a methylvinylsiloxy group and having a viscosity of 100,000 mPa·s at 25° C. | 100 weight parts |
| A linear organohydrogensiloxane containing 40 mol % of a methylhydrogensiloxane unit | 10 weight parts |
| Quartz | 50 weight parts |
| Vaseline | 100 weight parts |

(Catalyst Paste)

| | |
|---|---|
| A dimethylpolysiloxane wherein both molecular chain terminals are blocked with a methylvinylsiloxy group | 100 weight parts |
| A silicone oil solution containing 0.5% by weight of a platinum complex of 1,3-divinyltetramethyldisiloxane | 5 weight parts |
| Quartz | 50 weight parts |

A base paste and a catalyst paste were produced by vacuum-stirring the aforementioned each component by a planetary mixer. These base paste and catalyst paste were subjected to the same tests as Example 1. These results were shown in Table 1.

Comparative Example 2

The same various kinds of tests as Example 1 were carried out by using a commercial silicone impression material (product name: EXAHIFLEX REGULAR, produced by GC Corporation). These results were shown in Table 1.

TABLE 1

| | Examples | | | | Comparative examples | |
|---|---|---|---|---|---|---|
| | 1 | 2 | 3 | 4 | 1 | 2 |
| Hardness | 19 | 20 | 20 | 19 | 21 | 24 |
| Elastic strain (%) | 18.5 | 19.1 | 19.1 | 18.1 | 14 | 9.1 |
| * Viscosity of a kneaded material (mPa × s) | 320,000 | 240,000 | 410,000 | 310,000 | 10,000 | 20,000 |
| Easiness of removing an impression material | Removing was easy similar to an alginate impression material | Removing was easy similar to an alginate impression material | Removing was easy similar to an alginate impression material | Removing was easy similar to an alginate impression material | Removing was a little harder than that of an alginate impression material | The impression material could not be removed |

* The viscosity of the conventional alginate impression material is about 350,000 mPa·s.

As shown in Table 1, the dental impression material composition according to the present invention shown in the examples has high hardness and elastic strain, and removing force of a cured body is low similar to that of an alginate impression material. Further, viscosity of a kneaded material is similar to that of an alginate impression material, and the value of the viscosity is higher than that of a silicone composition having comparatively high elastic strain or that of a commercial product, where the silicone composition and the commercial product were shown as comparative examples. Thus, the dental silicone impression material composition according to the present invention can be used like an alginate impression material even though it is a silicone-based impression material. These properties are very effective for cases in which the silicone-based impression material has been hardly used, or cases which need complicated operations and cares.

What is claimed is:

1. A dental silicone impression material composition comprising:

A) 100 weight parts of an organopolysiloxane mixture comprising a) an organopolysiloxane having at least two aliphatic unsaturated hydrocarbons in one molecule and having viscosity of 1,000,000 mPa·s or more at 25° C., and b) an organopolysiloxane having at least one aliphatic unsaturated hydrocarbon in one molecule and having viscosity of 100 to 5,000 mPa·s at 25° C., wherein a ratio of a):b) is 1:0.5 to 3;

B) 0.1 to 100 weight parts of an organohydrogenpolysiloxane having at least three hydrogen atoms directly bonded to a silicon atom in one molecule with respect to 100 weight parts of the component A);

C) 10 ppm to 1 weight part of a silicone-soluble platinum compound with respect to the total amount of the two components A) and B);

D) 1 to 50 parts of an organopolysiloxane not having a functional group with respect to 100 weight parts of the component A); and E) 10 to 100 weight parts of an inorganic filler with respect to 100 weight parts of the component A).

* * * * *